United States Patent
Zoellner et al.

(10) Patent No.: US 10,862,052 B2
(45) Date of Patent: Dec. 8, 2020

(54) ELECTRICALLY DOPED ORGANIC SEMICONDUCTING MATERIAL AND ORGANIC LIGHT EMITTING DEVICE COMPRISING IT

(71) Applicant: Novaled GmbH, Dresden (DE)

(72) Inventors: Mike Zoellner, Dresden (DE); Omrane Fadhel, Dresden (DE); Ulrich Denker, Dresden (DE)

(73) Assignee: Novaled GmbH, Dresden (DE)

( * ) Notice: Subject to any disclaimer, the term of this patent is extended or adjusted under 35 U.S.C. 154(b) by 0 days.

(21) Appl. No.: 15/323,361

(22) PCT Filed: Jun. 26, 2015

(86) PCT No.: PCT/EP2015/064575
§ 371 (c)(1),
(2) Date: Dec. 30, 2016

(87) PCT Pub. No.: WO2016/001097
PCT Pub. Date: Jan. 7, 2016

(65) Prior Publication Data
US 2017/0162800 A1   Jun. 8, 2017

(30) Foreign Application Priority Data
Jun. 30, 2014   (EP) ................................ 14174910

(51) Int. Cl.
*H01L 51/00* (2006.01)
*H01L 51/50* (2006.01)
(Continued)

(52) U.S. Cl.
CPC ........ *H01L 51/0073* (2013.01); *C07D 311/96* (2013.01); *C07D 405/14* (2013.01);
(Continued)

(58) Field of Classification Search
CPC .......... H01B 1/12; H01B 1/121; H01B 1/122; H01B 1/20; H01L 51/005; H01L 51/0058;
(Continued)

(56) References Cited

U.S. PATENT DOCUMENTS

| | | | | |
|---|---|---|---|---|
| 7,014,925 | B2 * | 3/2006 | Thoms ................. | C07D 221/20 252/301.16 |
| 2003/0168970 | A1 * | 9/2003 | Tominaga ............... | C07C 15/28 313/504 |
| 2015/0295181 | A1 * | 10/2015 | Mujica-Fernaud ........................ | H01L 51/0052 252/500 |

FOREIGN PATENT DOCUMENTS

| CN | 101440082 A * | 5/2009 |
|---|---|---|
| CN | 103666454 A | 3/2014 |

(Continued)

OTHER PUBLICATIONS

English machine translation of CN-101440082-A (Year: 2009).*

(Continued)

*Primary Examiner* — Matthew R Diaz
(74) *Attorney, Agent, or Firm* — Eversheds Sutherland (US) LLP

(57) ABSTRACT

The invention relates to electrically doped semiconducting material comprising iii) at least one electrical dopant selected from metal salts consisting of at least one metal (Continued)

cation and at least one anion and iv) at least one matrix compound of formula 1

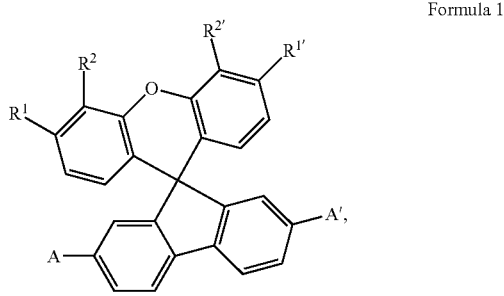

Formula 1 wherein each of $R^1$, $R^2$, $R^{1'}$, $R^{2'}$ is independently selected from H, $C_1$-$C_6$ alkyl, $C_1$-$C_6$ haloalkyl and $C_6$-$C_{14}$ aryl or both substituents on the same aromatic ring of the xanthene skeleton are hydrocarbyl groups linked with each other to form together an anelated divalent $C_2$-$C_{10}$ hydrocarbyl group and A and A' are independently selected from $C_1$-$C_{20}$ heteroaryl group comprising at least one $sp^2$ hybridized nitrogen atom as well as an electronic device and a compound.

15 Claims, 2 Drawing Sheets (51) Int. Cl.
*C07D 311/96* (2006.01)
*C07D 405/14* (2006.01)
(52) U.S. Cl.
CPC ........ *H01L 51/008* (2013.01); *H01L 51/5056* (2013.01); *H01L 51/5076* (2013.01); *H01L 51/5088* (2013.01); *H01L 51/5092* (2013.01); *H01L 51/5096* (2013.01); *H01L 2251/308* (2013.01); *H01L 2251/558* (2013.01)
(58) Field of Classification Search
CPC ............. H01L 51/0062; H01L 51/0073; H01L 51/0077; H01L 51/008; H01L 51/50; H01L 51/51; H01L 51/5012; H01L 51/5048; H01L 51/5052; H01L 51/5056; H01L 51/506; H01L 51/5068; H01L 51/5072; H01L 51/5076; H01L 51/5084; H01L 51/5088; H01L 51/5092; H01L 51/5096; H01L 2251/308; H01L 2251/50; H01L 2251/53; H01L 2251/5338; H01L 2251/5346; H01L 2251/5353; H01L 2251/5361; H01L 2251/558; H01L 51/0065; C07D 311/96; C07D 405/14
See application file for complete search history.

(56) References Cited

FOREIGN PATENT DOCUMENTS

| JP | 2009-191232 A | 8/2009 | |
|---|---|---|---|
| JP | 2009191232 A | 8/2009 | |
| WO | 2013/079676 A1 | 6/2013 | |
| WO | 2013/079678 A1 | 6/2013 | |
| WO | 2013/149958 A1 | 10/2013 | |
| WO | WO-2014072017 A1 * | 5/2014 | ......... H01L 51/0052 |

OTHER PUBLICATIONS

PCT International Search Report and Written Opinion for PCT Application No. PCT/EP2015/064575 dated Sep. 28, 2015.
Chinese Office Action for CN Application No. 201580035807 dated Feb. 11, 2018 (9 pages).
PCT International Preliminary Report on Patentability for PCT Application No. PCT/EP2015/064575 dated Jan. 12, 2017 (6 pages).
Taiwanese Office Action for TW Application No. 104120939 dated May 22, 2019 (3 pages, English translation).

* cited by examiner

ELECTRICALLY DOPED ORGANIC SEMICONDUCTING MATERIAL AND ORGANIC LIGHT EMITTING DEVICE COMPRISING IT

CROSS REFERENCE TO RELATED APPLICATIONS

This application is a U.S. national stage application of PCT/EP2015/064575, filed Jun. 26, 2015, which claims priority to European Application No. 14174910.1, filed Jun. 30, 2014. The contents of these applications are hereby incorporated by reference.

The present invention concerns organic semiconducting material with improved electrical properties, electronic device utilizing the improved electrical properties of the inventive semiconducting material and particular compound suitable for this organic semiconducting material.

I. BACKGROUND OF THE INVENTION

Some xanthene compounds for use as fluorescent compounds in organic electroluminescence devices were disclosed in JP5416906. Our previous application published as WO2013/149958 and incorporated herein by reference disclosed specifically substituted spiroxanthene compounds as suitable electron transport matrices for organic electronic devices, particularly for electron transport layers (ETLs) in organic light emitting diodes (OLEDs). This application also successfully proved electrical n-doping in the disclosed spiroxanthene matrices using very strong redox n-dopants like $W_2(hpp)_4$.

Despite technical solutions for safe and reproducible handling with extremely air-sensitive strong reduction agents like $W_2(hpp)_4$ are known, see e.g. WO 2007/065685, using these complex dopants requiring additional technical measures in mass production raises costs significantly.

Metal salt additives are known as an air stable alternative to the strongly reductive n-dopants for electrical n-doping in certain organic matrices. Specifically, matrices comprising highly polar groups, like the phosphine oxide group, are specifically suitable for electrical n-doping with metal salt additives, see e.g. EP 13 170 862 or EP 13 187 905. Most frequently used metal salt n-doping additives are lithium salts. Specifically, chelates like lithium 8-hydroxyquinolinolate (LiQ) are used, see e.g. WO 2012/173370. Nevertheless, there is still an unmet demand for air stable semiconducting materials having high performance in electronic devices and preparable easily and with high reproducibility in state-of-the-art equipment for mass production.

It is an object of the invention to provide alternative materials for electronic devices having low operational voltage and high efficiency, specifically, for OLEDs with a low operational voltage, good power efficiency and, simultaneously, with good thermal characteristics.

It is a further object of the invention to utilize these alternative materials in electronic devices, specifically in OLEDs.

A third object of the invention is to provide new compounds specifically suitable for the first and second object of the invention.

II. SUMMARY OF THE INVENTION

The first object is achieved by electrically doped semiconducting material comprising i) at least one electrical dopant selected from metal salts consisting of at least one metal cation and at least one anion and ii) at least one matrix compound of formula 1

Formula 1 wherein each of $R^1$, $R^2$, $R^{1'}$, $R^{2'}$ is independently selected from H, $C_1$-$C_6$ alkyl, $C_1$-$C_6$ haloalkyl and $C_6$-$C_{14}$ aryl or both substituents on the same aromatic ring of the xanthene skeleton are hydrocarbyl groups linked with each other to form together an anelated divalent $C_2$-$C_{10}$ hydrocarbyl group and A and A' are independently selected from $C_1$-$C_{20}$ heteroaryl group comprising at least one $sp^2$ hybridized nitrogen atom.

It is understood that the alkyl can be straight or branched and may comprise a ring structure.

Examples of alkyl substituents are methyl, ethyl, propyl, isopropyl, butyl, cyclopentyl, cyclohexyl. Specific examples of halogenated alkyls are perfluorinated alkyls like trifluoromethyl, perfluoroethyl, perfluor-t-butyl. The aryl comprises at least one aromatic ring and can be substituted or unsubstituted. It is understood that if any substituents are present, they are included in the overall count of the carbon atoms. Examples of aryls are phenyl, naphtyl, tolyl, xylyl, tert-butylphenyl, biphenylyl, fluorenyl. Preferred aryls comprise one or two aromatic rings.

Preferred are compounds of the formula 1 wherein the substituents having the same denomination differing only by the prime sign, e.g. $R^1$ and $R^{1'}$, are the same. More preferred are the matrix compounds wherein $R^1$, $R^2$, $R^{1'}$, $R^{2'}$ is H, or $R^1$ with $R^2$ and $R^{1'}$ with $R^{2'}$ form anelated benzo-rings. Even preferred are the matrix compounds wherein, in the formula 1, A and A' are selected from pyridyl and quinolinyl. Specific examples of pyridyl are 2-pyridyl, 3-pyridyl and 4-pyridyl, examples of quinolinyl are quinoline-2-yl and quinoline-3-yl. Other examples of suitable nitrogen-containing heteroaryls are diazinyls, triazinyls, diazolyls, triazolyls and tetrazolyls. The term "anelated benzo-ring" can be explained on the compounds C7 and C6 of examples given below. C7 can be seen as a derivative of the compound C6, wherein $R^1$ with $R^2$ and $R^{1'}$ with $R^{2'}$ form anelated benzo-rings.

Preferred metal salts are salts comprising cations of metals in oxidation state I or II. More preferred are salts, wherein the metal cation is selected from cations of alkali metals or from cations of alkaline earth metals. Even more preferred are metal salts, wherein the metal cation is $Li^+$ or $Mg^{2+}$. Most preferred are lithium salts.

As regards metal salt anions, preferred are salts selected from i) metal complexes comprising a 5-, 6- or 7-membered ring that contain the metal cation attached to other atoms of the ring through atoms independently selected from nitrogen and oxygen and ii) metal complexes having the structure according to formula (I)

Formula (I)

wherein $A^1$ is a $C_6$-$C_{30}$ arylene or $C_2$-$C_{30}$ heteroarylene comprising at least one atom selected from O, S and N in an aromatic ring and each of $A^2$ and $A^3$ is independently selected from a $C_6$-$C_{30}$ aryl and $C_2$-$C_{30}$ heteroaryl comprising at least one atom selected from O, S and N in an aromatic ring.

Examples for chelates mentioned under point i) are lithium acetylacetonate or lithium 8-hydroxyquinolinolate (D1)

D1

Additives according to formula (I) were disclosed in WO2013/079678 and in EP 13 170 862, as examples can serve compounds D2 and D3

D2

D3

More preferred are the salts selected from lithium salts comprising an anion having formula (II)

Formula (II)

wherein each of $G^1$-$G^4$ is independently selected from H, substituted or unsubstituted $C_6$-$C_{20}$ aryl and substituted or unsubstituted $C_2$-$C_{20}$ heteroaryl.

Even more preferred are salts of formula (II), wherein at least two of substituents $G^1$-$G^4$ are pyrazolyl.

Use of compounds of formula (II) as ETL additives is disclosed e.g. in WO2013/079676, an example is compound D4

D4

The electrically doped semiconducting material can contain as much as 5 mol or more of the metal salt additive per 1 mol matrix (in case of polymeric matrix, per 1 mol of polymer building units having charge transport function). Preferably, it contains less than 5 mol additive per 1 mol matrix, more preferably less than 4 mol additive per 1 mol matrix, even more preferably less than 3 mol additive per 1 mol matrix, most preferably less than 2.5 mol additive per 1 mol matrix.

The additive content may be less than 0.5 mol per 1 mol matrix, preferably it is 0.5 mol per 1 mol matrix or higher, more preferably 1 mol per 1 mol matrix or higher, most preferably 1.5 mol per 1 mol matrix or higher.

The second object of the invention is achieved by an electronic device comprising between cathode and anode the semiconducting material according to invention.

Preferably, the inventive semiconducting material forms a layer adjacent to the cathode. More preferably, the device comprises a light emitting layer between the anode and the cathode, wherein the inventive electrically doped semiconducting material forms a layer between the cathode and the emitting layer.

In one of preferred embodiments, the layer of the inventive electrically doped semiconducting material is adjacent to the emitting layer.

In another embodiment, a hole blocking layer is provided between the layer of the inventive electrically doped semiconducting material and the emitting layer.

It may be provided that the electron transporting layer is thin, with a nominal thickness of less than 50 nm, preferably less than 40 nm, more preferably less than 30 nm, even more preferably less than 20 nm, even more preferably less than 15 nm, most preferably less than 10 nm, still but less preferably less than 7 nm.

The layer of the inventive semiconducting material is thicker than 1 nm, preferably thicker than 2 nm, more preferably thicker than 3 nm, even more preferably thicker than 4 nm, most preferably at least 5 nm thick.

Third object of the invention is achieved by compound having the structure given by formula

III. ADVANTAGEOUS EFFECT OF THE INVENTION

Table 1 summarizes results from device experiments described in more detail in examples. It shows that spiroxanthene compounds comprising nitrogen containing heterocyclic substituents as specified above, form with metal additives semiconducting materials allowing very good charge injection in organic electronic devices.

TABLE 1

| code | formula | Matrix:additive wt ratio | Voltage (V) @ 10 mA/cm$^2$ | QE (%) @ 1000 cd/m$^2$ |
|---|---|---|---|---|
| E1 |  | 80:20<br>65:35 | 8.3<br>7.3 | 3.8<br>5.0 |
| E2 |  | 80:20 | >10 | n/a |
| E3 |  | 70:30 | >10 | n/a |
| E4 |  | 70:30 | 7.7 | 5.5 |

TABLE 1-continued

| code | formula | Matrix:additive wt ratio | Voltage (V) @ 10 mA/cm$^2$ | QE (%) @ 1000 cd/m$^2$ |
|---|---|---|---|---|
| E5 |  | 80:20<br>60:40 | >10<br>>10 | n/a<br>n/a |
| C2 |  | 65:35 | 4.8 | 7.2 |
| C5 |  | 70:30<br>90:10 | 5.1<br>5.6 | 8.5<br>7.9 |
| C6 |  | 80:20<br>70:30<br>65:35<br>45:55 | 3.5<br>3.9<br>3.6<br>3.6 | 5.7<br>7.4<br>6.8<br>6.9 |
| C7 |  | 65:35 | 3.7 | 6.5 |

V. DETAILED DESCRIPTION OF THE INVENTION

Device Architecture

Figure 1:
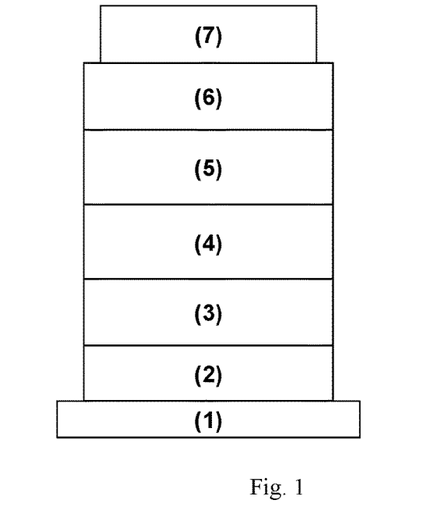
FIG. 1 shows a schematic illustration of a device in which the present invention can be incorporated.

FIG. 1 shows the scheme of experimental blue OLED used in Example 1 for the comparison of the inventive semiconducting materials with analogous materials comprising xanthene-based matrix compounds that lack nitrogen containing heterocyclic substituents.

The skilled person can design devices for other purposes by choosing the supporting materials known in the art, layer thicknesses, deposition methods and other parameters appropriately.

For example, other layers can be inserted between those depicted, or some layers may be omitted. Following short overview has only informative character and does not limit the scope of the invention.

Substrate

It can be flexible or rigid, transparent, opaque, reflective, or translucent. The substrate should be transparent or translucent if the light generated by the OLED is to be transmitted through the substrate (bottom emitting). The substrate may be opaque if the light generated by the OLED is to be emitted in the direction opposite of the substrate, the so called top-emitting type. The OLED can also be transparent. The substrate can be either arranged adjacent to the cathode or anode.

Electrodes

The electrodes are the anode and the cathode, they must provide a certain amount of conductivity, being preferentially conductors. In OLEDs, at least one of the electrodes must be semi-transparent or transparent to enable the light transmission to the outside of the device. Typical electrodes are layers or a stack of layer, comprising metal and/or transparent conductive oxide. Other possible electrodes are made of thin busbars (e.g. a thin metal grid) wherein the spaces between the busbars is filled (coated) with a transparent material with a certain conductivity, such as graphene, carbon nanotubes, doped organic semiconductors, etc.

In one mode, the anode is the electrode closest to the substrate, which is called non-inverted structure. In another mode, the cathode is the electrode closest to the substrate, which is called inverted structure.

Typical materials for the anode are indium tin oxide (ITO) and Ag. Typical materials for the cathode are magnesium-silver alloy (10 vol. % Mg), Ag, ITO, aluminium. Mixtures and multilayer are also possible.

Hole Transporting Layer (HTL)

It is a layer comprising a large gap semiconductor responsible to transport holes from the anode or holes from a CGL to the emitting layer (EML). The HTL is comprised between the anode and the EML or between the hole generating side of a CGL and the LEL. The HTL can be doped with a p-dopant. P-doping the HTL lowers its resistivity and avoids the respective power loss due to the otherwise high resistivity of the undoped semiconductor. The doped HTL can also be used as optical spacer, because it can be made very thick, up to 1000 nm or more without significant increase in resistivity.

Hole Injecting Layer (HIL)

It is a layer which facilitates the injection of holes from the anode or from the hole generating side of a CGL into an adjacent HTL. Typically the HIL is a very thin layer (<10 nm). The hole injection layer can be a pure layer of p-dopant and can be about 1 nm thick. When the HTL is doped, an HIL may not be necessary, since the injection function is already provided by the HTL.

Suitable compounds for the hole transport matrix material of the hole transport layer may be selected from the known hole transport matrices (HTMs), e.g. from triaryl amine compounds. Preferred HTMs for the inventive doped hole transport material are compounds comprising a conjugated system of delocalized electrons, wherein the conjugated system comprises lone electron pairs of at least two tertiary amine nitrogen atoms. Examples are N4,N4'-di(naphthalen-1-yl)-N4,N4'-diphenyl-[1,1'-biphenyl]-4,4'-diamine (HT1), and N4,N4, N4",N4"-tetra([1,1'-biphenyl]-4-yl)-[1,1':4',1"-terphenyl]-4,4"-diamine (HT2). The synthesis of terphenyl-diamine HTMs is described e.g. in WO2011/134458, US2012/223296 or WO2013/135237; 1,3-phenylenedi-amine matrices are described e.g. in WO2014/060526.

These documents are herein incorporated by reference. Many triaryl amine HTMs are commercially available.

Emitting Layer (EML)

The light emitting layer must comprise at least one emitter and can optionally comprise additional layers. A mixture of different types of emitters can be provided for higher efficiency. Mixed light can be realized by using emission from an emitter host and an emitter dopant.

Blocking layers can be used to improve the confinement of charge carriers in the EML, as explained e.g. in U.S. Pat. No. 7,074,500 B2.

Electron Transporting Layer (ETL)

It is a layer comprising a large gap semiconductor responsible to transport electrons from the cathode or electrons from a CGL to the ETL. The ETL is comprised between the anode and the EML or between the electron generating side of a CGL and the LEL. The ETL can be mixed with an electrical n-dopant, in which case it is said the ETL is n-doped. The ETL can be comprised by several layers, which can have different compositions. Electrical n-doping the ETL lowers its resistivity and/or improves its ability to inject electrons into an adjacent layer and avoids the respective power loss due to the otherwise high resistivity (and/or bad injection ability) of the undoped semiconductor. The doped ETL can also be used as optical spacer, because it can be made very thick, up to 1000 nm or more without significant increase in resistivity.

Hole blocking layers and electron blocking layers can be employed as usual.

Charge Generation Layer (CGL)

The OLED can comprise a CGL which can be used in conjunction with an electrode as inversion contact, or as connecting unit in stacked OLEDs. A CGL can have the most different configurations and names, examples are pn-junction, connecting unit, tunnel junction, etc. Best examples are pn junctions as disclosed in US 2009/0045728 A1, US 2010/0288362 A1. Metal layers and or insulating layers can also be used.

Stacked OLEDs

When the OLED comprises two or more EMLs separated by CGLs, the OLED is named a stacked OLED, otherwise it is named a single unit OLED. The group of layers between two closest CGLs or between one of the electrodes and the closest CGL is named a electroluminescent unit (ELU). Therefore a stacked OLED can be described as anode/$ELU_1$/$\{CGL_X/ELU_{1+X}\}_X$/cathode, wherein x is a positive integer and each $CGL_X$ or each $ELU_{1+X}$ can be equal or different. The CGL can also be formed by the adjacent layers of two ELUs as disclosed in US2009/0009072 A1. Further stacked OLEDs are explained e.g. in US 2009/0045728 A1, US 2010/0288362 A1, and references therein.

Deposition of Organic Layers

Any organic semiconducting layers of the inventive display can be deposited by known techniques, such as vacuum thermal evaporation (VTE), organic vapour phase deposition, laser induced thermal transfer, spin coating, blade coating, slot dye coating, inkjet printing, etc. A preferred method for preparing the OLED according to the invention is vacuum thermal evaporation.

Preferably, the ETL is formed by evaporation. When using an additional material in the ETL, it is preferred that the ETL is formed by co-evaporation of the electron transporting matrix (ETM) and the additional material. The additional material may be mixed homogeneously in the ETL. In one mode of the invention, the additional material has a concentration variation in the ETL, wherein the concentration changes in the direction of the thickness of the stack of layers. It is also foreseen that the ETL is structured in sub-layers, wherein some but not all of these sub-layers comprise the additional material.

Electrical Doping

The present invention can be used in addition or in combination with electrical doping of organic semiconducting layers.

The most reliable and at the same time efficient OLEDs are OLEDs comprising electrically doped layers. Generally, the electrical doping means improving of electrical properties, especially the conductivity and/or injection ability of a doped layer in comparison with neat charge-transporting matrix without a dopant. In the narrower sense, which is usually called redox doping or charge transfer doping, hole transport layers are doped with a suitable acceptor material (p-doping) or electron transport layers with a donor material (n-doping), respectively. Through redox doping, the density of charge carriers in organic solids (and therefore the conductivity) can be increased substantially. In other words, the redox doping increases the density of charge carriers of a semiconducting matrix in comparison with the charge carrier density of the undoped matrix. The use of doped charge-carrier transport layers (p-doping of the hole transport layer by admixture of acceptor-like molecules, n-doping of the electron transport layer by admixture of donor-like molecules) in organic light-emitting diodes is, e.g., described in US 2008/203406 and U.S. Pat. No. 5,093,698.

US2008227979 discloses in detail the charge-transfer doping of organic transport materials, with inorganic and with organic dopants. Basically, an effective electron transfer occurs from the dopant to the matrix increasing the Fermi level of the matrix. For an efficient transfer in a p-doping case, the LUMO energy level of the dopant is preferably more negative than the HOMO energy level of the matrix or at least slightly more positive, not more than 0.5 eV, to the HOMO energy level of the matrix. For the n-doping case, the HOMO energy level of the dopant is preferably more positive than the LUMO energy level of the matrix or at least slightly more negative, not lower than 0.5 eV, to the LUMO energy level of the matrix. It is further more desired that the energy level difference for energy transfer from dopant to matrix is smaller than +0.3 eV.

Typical examples of known redox doped hole transport materials are: copperphthalocyanine (CuPc), which HOMO level is approximately −5.2 eV, doped with tetrafluoro-tetracyanoquinonedimethane (F4TCNQ), which LUMO level is about −5.2 eV; zincphthalocyanine (ZnPc) (HOMO=−5.2 eV) doped with F4TCNQ; a-NPD (N,N'-Bis(naphthalen-1-yl)-N,N'-bis(phenyl)-benzidine) doped with F4TCNQ. a-NPD doped with 2,2'-(perfluoronaphthalene-2,6-diylidene) dimalononitrile (PD1). a-NPD doped with 2,2',2"-(cyclopropane-1,2,3-triylidene)tris(2-(p-cyanotetrafluorophenyl)acetonitrile) (PD2). All p-doping in the device examples of the present application was done with 5 mol. % of PD2. Typical examples of known redox doped electron transport materials are: fullerene C60 doped with acridine orange base (AOB); perylene-3,4,9,10-tetracarboxylic-3,4,9,10-dianhydride (PTCDA) doped with leuco crystal violet; 2,9-di(phenanthren-9-yl)-4,7-diphenyl-1,10-phenanthroline doped with tetrakis (1,3,4,6,7,8-hexahydro-2H-pyrimido[1,2-a]pyrimidinato) ditung-sten (II) (W$_2$(hpp)$_4$); naphthalene tetracarboxylic acid di-anhydride (NTCDA) doped with 3,6-bis-(dimethyl amino)-acridine; NTCDA doped with bis (ethylene-dithio) tetrathiafulvalene (BEDT-TTF).

In devices demonstrating the present invention, redox doping has been used in the HTL.

Preferred ETL matrix compounds of the present invention are

C2

C5

C6

-continued

C7

C6 and C7 are the most preferred compounds.

VI. EXAMPLES

Synthesis Procedures

All manipulations were carried out under argon in thoroughly dried glass vessels, without any further purification of commercial chemicals except for the use of dried and degassed solvents (solvent purification system (SPS) quality).

General synthesis procedure, syntheses of precursor compounds, and syntheses of inventive C2, C and C6 as well as of comparative compounds were reported in WO2013/14998. Inventive compound C7 has been synthesized analogously and characterized as follows: TLC (silica, ethyl acetate): $R_f$=0.25

DSC: Melting point: 345° C. (peak), sublimed material

Glass transition Tg: 163° C. (onset), heating rate 10 K/min, sublimed material $^1$H-NMR (CD$_2$Cl$_2$ referenced to 5.31 ppm, 500.13 MHz): J[ppm]=6.50 ("d", J=8.5 Hz, 2H), 7.19 ("dd", J=8.0 Hz, 5.0 Hz, 2H), 7.32 ("d", J=9.0 Hz, 2H), 7.42 ("d", J=2.0 Hz, 2H, fluorene H-1'), 7.58 ("t" with fine splitting, J=7.5 Hz, 2H, xanthene H-2 or H-3), 7.70 ("t", J=2.0 Hz, 2H), 7.72 (signal pattern not clear due to overlapping signals, 2H), 7.73 ("ddd", J=8.0 Hz, 7.0 Hz, 1.0 Hz, 2H, xanthene H-2 or H-3), 7.78 ("d", J=8.0 Hz, 2H), 8.06 ("d", J=8.0 Hz, 2H), 8.42 ("dd", J=4.5 Hz, 1.5 Hz, 2H), 8.68 ("d", J=2.5 Hz, 2H, pyridine H-2), 8.82 ("d", J=8.5 Hz, 2H, pyridine H-6).

$^{13}$C-NMR (CD$_2$Cl$_2$ referenced to 53.73 ppm, 125.76 MHz): δ [ppm]=54.82 (s, spiro-sp$^3$ C), 117.72, 121.27, 121.93, 123.49, 123.56, 124.90, 125.14, 125.61, 126.68, 127.10, 127.53, 127.87, 133.93, 134.23, 136.15, 138.73, 139.54, 146.18, 148.36, 148.79, 157.56 (d, C$_{Ar}$—O).

Example 1

A bottom emitting blue OLED schematically shown in shown in FIG. 1 was fabricated by standard vacuum thermal evaporation (VTE) technique. On a glass substrate (not shown) provided with a 90 nm thick ITO anode (1), following layers were deposited subsequently:

(2) 10 nm thick hole injecting and hole transporting layer consisting of hole transport matrix HT1 and p-dopant 2,2', 2"-(cyclopropane-1,2,3-triylidene)tris(2-(p-cyanotetrafluorophenyl)acetonitrile) (PD2) in a weight ratio 92:8, (3) 120 nm thick hole transporting and electron blocking layer of HT1, (4) 20 nm thick emitting layer consisting of the commercially available host ABH113 and emitter NUBD370 (both from SFC, Korea), (5) 31 nm thick hole blocking layer made of compound E1, (6) 5 nm thick electron injecting and electron transporting layer consisting of the inventive or comparative compounds given in the Table 1 co-deposited with the additive D4 in the weight ratio given in the Table 1, and (7) 100 nm thick aluminium cathode.

Figure 2:
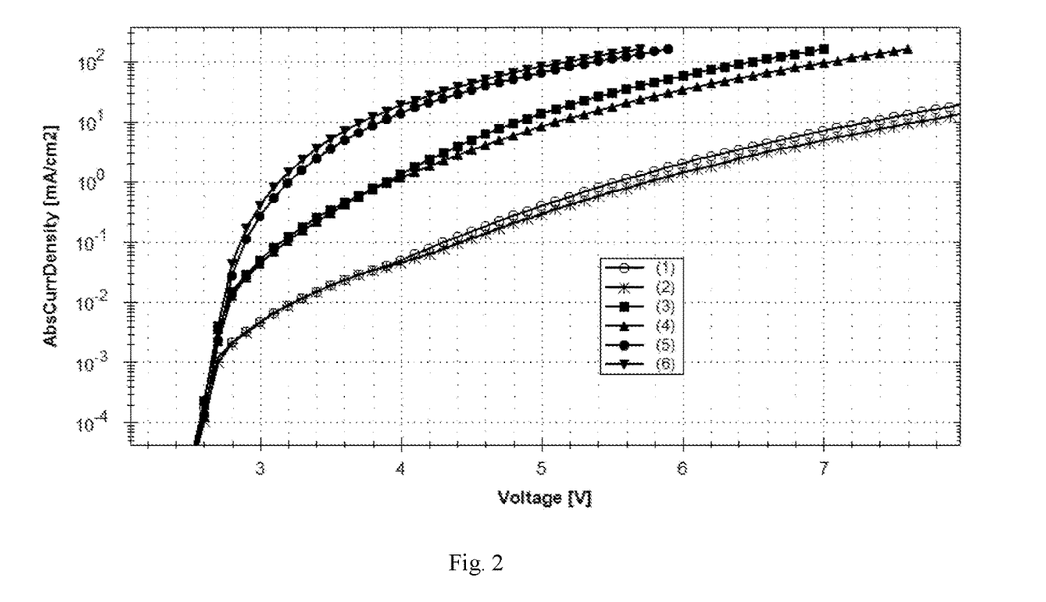
FIG. 2 shows the current density versus the applied bias of in devices of Example 1.
Figure 3:
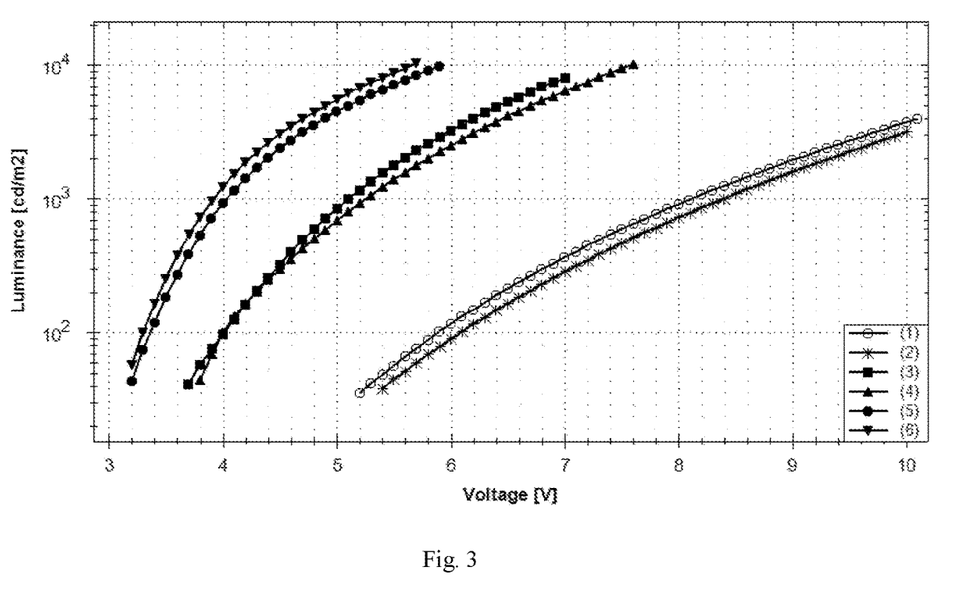
FIG. 3 shows the density of the luminous intensity versus the applied bias in devices of Example 1.

In FIGS. 2 and 3, the curve (1) refers to compound E1, (2) refers to compound E4, (3) refers to compound C2, (4) refers to compound C5, (5) refers to compound C6 and (6) refers to compound C7. The compounds were co-deposited with either 30% or 35% (in weight ratio) of compound D4. It is clearly seen that OLEDs comprising the inventive doped semiconducting materials perform well only if they comprise the xanthene matrices substituted with nitrogen containing substituents as defined in this invention.

The voltages and efficiencies reported in the Table 1 show that xanthene matrices comprising nitrogen-containing heterocyclic substituent as specified above can be, oppositely to other xanthene matrices having very similar structures and frontier orbital energy levels, successfully doped with air stable metal salt n-dopants.

The features disclosed in the foregoing description, in the claims and the accompanying drawings may, both separately and in any combination thereof, be material for realizing the invention in diverse forms thereof.

Used Abbreviations

DSC differential scanning calorimetry
Fc$^+$/Fc ferrocenium/ferrocene reference system
HPLC high performance liquid chromatography
SPS solvent purification system
TLC thin layer chromatography
UV UV/Vis spectroscopy
eq chemical equivalent
mol. % molar percent
vol. % volume percent

The invention claimed is:
1. An electrically doped semiconducting material comprising
    i) at least one electrical dopant selected from metal salts consisting of at least one metal cation and at least one anion and
    ii) at least one matrix compound of formula 1

Formula 1 wherein each of R$^1$, R$^2$, R$^{1'}$, R$^{2'}$ is independently selected from the group consisting of H, C$_1$-C$_6$ alkyl, C$_1$-C$_6$ haloalkyl, and C$_6$-C$_{14}$ aryl, or both substituents on the same aromatic ring of the xanthene skeleton are hydrocarbyl groups linked with each other to form together an anelated divalent C$_2$-C$_{10}$ hydrocarbyl group, and A and A' are selected from a $C_1$-$C_{20}$ heteroaryl group comprising at least one sp² hybridized nitrogen atom; wherein $R^1$ and $R^{1'}$ are the same, $R^2$ and $R^{2'}$ are the same, and A and A' are the same; and wherein a) the metal salt is selected from metal complexes comprising a 5-, 6- or 7-membered ring that contains the metal cation attached to other atoms of the ring through atoms independently selected from nitrogen and oxygen; or b) the metal salt is a metal complex having the structure according to formula (I)

Formula (I)

wherein $A^1$ is a $C_6$-$C_{30}$ arylene or $C_2$-$C_{30}$ heteroarylene comprising at least one atom selected from O, S, or N in an aromatic ring and each of $A^2$ and $A^3$ is independently selected from a $C_6$-$C_{30}$ aryl or $C_2$-$C_{30}$ heteroaryl comprising at least one atom selected from O, S, or N in an aromatic ring; or c) the metal salt is selected from lithium salts comprising an anion having formula (II)

Formula (II)

wherein each of $G^1$-$G^4$ is independently selected from H, substituted or unsubstituted $C_6$-$C_{20}$ aryl, or substituted or unsubstituted $C_2$-$C_{20}$ heteroaryl; and wherein the metal cation is Li⁺.

2. The electrically doped semiconducting material according to claim 1, wherein A and A' are selected from the group consisting of pyridyl and quinolinyl.

3. The electrically doped semiconducting material according to claim 1, wherein at least two of substituents $G^1$-$G^4$ are pyrazolyl.

4. An electronic device comprising the electrically doped semiconducting material of claim 1 between a cathode and an anode.

5. The electronic device according to claim 4, wherein the electrically doped semiconducting material forms a layer adjacent to the cathode.

6. The electronic device according to claim 5, wherein the layer of the electrically doped semiconducting material has a thickness less than 50 nm.

7. The electronic device according to claim 5, wherein the layer of the electrically doped semiconducting material has a thickness less than 40 nm.

8. The electronic device according to claim 5, wherein the layer of the electrically doped semiconducting material has a thickness less than 30 nm.

9. The electronic device according to claim 5, wherein the layer of the electrically doped semiconducting material has a thickness less than 20 nm.

10. The electronic device according to claim 5, wherein the layer of the electrically doped semiconducting material has a thickness less than 15 nm.

11. The electronic device according to claim 5, wherein the layer of the electrically doped semiconducting material has a thickness less than 10 nm.

12. The electronic device according to claim 5, wherein the layer of the electrically doped semiconducting material has a thickness less than 7 nm.

13. The electronic device according to claim 4 further comprising a light emitting layer between the anode and the cathode, wherein the electrically doped semiconducting material forms a layer between the cathode and the light emitting layer.

14. The electronic device according to claim 13, wherein the electrically doped semiconducting material forms a layer adjacent to the light emitting layer.

15. The electronic device according to claim 13, wherein a hole blocking layer is provided between the light emitting layer and the layer of the electrically doped semiconducting material.

* * * * *